United States Patent
Joseph et al.

(10) Patent No.: US 9,999,761 B2
(45) Date of Patent: Jun. 19, 2018

(54) EXTRACORPOREAL MEMBRANE OXYGENATION CANNULA HEMOSTATIC PLUG

(71) Applicant: Jumark Properties, LLC, Durham, NC (US)

(72) Inventors: Mark Joseph, Durham, NC (US); Kenneth Jose Addison, Chapel Hill, NC (US)

(73) Assignee: Jumark Properties LLC, Durham, NC (US)

( * ) Notice: Subject to any disclaimer, the term of this patent is extended or adjusted under 35 U.S.C. 154(b) by 0 days. days.

(21) Appl. No.: 14/334,859

(22) Filed: Jul. 18, 2014

(65) Prior Publication Data
US 2016/0015955 A1    Jan. 21, 2016

(51) Int. Cl.
*A61M 39/06* (2006.01)
*A61M 1/36* (2006.01)

(52) U.S. Cl.
CPC ...... *A61M 39/0606* (2013.01); *A61M 1/3659* (2014.02); *A61M 2039/062* (2013.01); *A61M 2039/0633* (2013.01)

(58) Field of Classification Search
CPC .............. A61M 39/06; A61M 39/0606; A61M 2039/062; A61M 2039/0626; A61M 2039/064; A61M 1/3659
See application file for complete search history.

(56) References Cited

U.S. PATENT DOCUMENTS

| | | | | |
|---|---|---|---|---|
| 4,000,739 A | * | 1/1977 | Stevens | A61M 25/00 600/433 |
| 4,430,081 A | * | 2/1984 | Timmermans | A61M 39/0606 251/149.1 |
| 4,610,665 A | * | 9/1986 | Matsumoto | A61M 39/0606 604/167.04 |
| 4,712,705 A | * | 12/1987 | Fuehrer | B65D 41/48 215/254 |
| 4,813,937 A | * | 3/1989 | Vaillancourt | A61M 5/145 128/DIG. 12 |

(Continued)

OTHER PUBLICATIONS

Sandham, John (Compiled/edited), Extracorporeal Membrane Oxygenation (ECMO), Electro-Biomedical Engineering UK website, http://www.ebme.co.uk/articles/clinical-engineering/33-extracorporeal-membrane-oxygenation-ecmo.

(Continued)

*Primary Examiner* — Andrew Gilbert
(74) *Attorney, Agent, or Firm* — Blank Rome LLP; Michael C. Greenbaum; Tara L. Marcus

(57) ABSTRACT

The present invention is a hemostatic plug for use with Extracorporeal Membrane Oxygenation (ECMO) cannulas that allow quick access to the blood vessel as well as maintaining a sterile environment to resume ECMO, if needed. It is designed to be a universal fit for use with adult ECMO circuits. The plug consists of a hemostatic membrane, a collection chamber and a cap. The membrane is designed to allow catheter delivery of up to a 19 French diameter through the ECMO cannula. The collection chamber allows the distribution of blood pressure over a broader surface, which allows additional hemostasis in addition to the membranes. The plug is then further reinforced with a cap that provides additional hemostasis, but when removed, allows hemostatic access into the blood vessel via the ECMO cannula.

7 Claims, 5 Drawing Sheets

(56) References Cited

U.S. PATENT DOCUMENTS

| | | | | |
|---|---|---|---|---|
| 4,889,137 A | * | 12/1989 | Kolobow | A61F 2/88 128/898 |
| 4,991,629 A | * | 2/1991 | Ernesto | A61M 39/20 138/89 |
| 5,000,745 A | * | 3/1991 | Guest | A61M 39/0606 251/149.1 |
| 5,009,636 A | * | 4/1991 | Wortley | A61M 25/007 604/43 |
| 5,053,013 A | * | 10/1991 | Ensminger | A61M 39/0208 604/167.04 |
| 5,125,903 A | * | 6/1992 | McLaughlin | A61M 39/0606 137/849 |
| 5,186,713 A | * | 2/1993 | Raible | A61M 1/1698 604/6.14 |
| 5,267,966 A | * | 12/1993 | Paul | A61M 39/0606 137/845 |
| 5,267,996 A | * | 12/1993 | Fletcher | A61B 5/0084 604/35 |
| 5,694,978 A | * | 12/1997 | Heilmann | F16L 55/1152 138/103 |
| 5,935,122 A | * | 8/1999 | Fourkas | A61B 17/3462 604/249 |
| 6,165,168 A | * | 12/2000 | Russo | A61M 39/045 604/247 |
| 6,325,785 B1 | * | 12/2001 | Babkes | A61M 1/0001 128/202.27 |
| 6,610,031 B1 | * | 8/2003 | Chin | A61M 39/045 604/167.04 |
| 6,911,025 B2 | * | 6/2005 | Miyahara | A61M 39/162 604/415 |
| 7,081,106 B1 | * | 7/2006 | Guo | A61M 39/06 251/149.1 |
| 7,799,046 B2 | | 9/2010 | White et al. | |
| 8,114,102 B2 | | 2/2012 | Galdonik et al. | |
| 8,608,711 B2 | * | 12/2013 | Lee | A61M 5/162 604/249 |
| 8,726,931 B2 | * | 5/2014 | Buiser | F16K 15/147 137/512.15 |
| 2001/0041872 A1 | * | 11/2001 | Paul, Jr. | A61M 39/0606 604/167.04 |
| 2007/0060902 A1 | * | 3/2007 | Brandenburger | A61J 1/10 604/403 |
| 2008/0009783 A1 | * | 1/2008 | Branderburger | A61M 39/20 604/30 |
| 2011/0230821 A1 | | 9/2011 | Babic | |
| 2012/0220955 A1 | * | 8/2012 | Maseda | A61M 39/16 604/256 |
| 2013/0030414 A1 | * | 1/2013 | Gardner | A61M 39/20 604/533 |

OTHER PUBLICATIONS

En.wikipedia.org, Extracorporeal Membrane Oxygenation, http://en.wikipedia.org/wiki/Extracorporeal_membrane_oxygenation.

* cited by examiner

EXTRACORPOREAL MEMBRANE OXYGENATION CANNULA HEMOSTATIC PLUG

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a system for use with an extracorporeal membrane oxygenation (ECMO) cannula (catheter). In particular, the present invention is a hemostatic plug for use with an ECMO cannula which is a universal fit for adult size cannulas.

Description of Related Art

ECMO provides temporary life support to patients usually with reversible cardiac or respiratory failure. The method delivers oxygen by extracorporeal measures by mechanical bypass that takes place outside the body of the person being treated. It is generally designed or intended for a patient whose heart and lungs cannot perform normally on their own.

Cannulas are placed in large blood vessels to provide access to and from the patient's blood. Anticoagulant drugs, such as heparin, are utilized to prevent the patient's blood from clotting. An ECMO circuit then pumps blood from the patient through a membrane oxygenator that mimics the gas exchange process of the lungs by removing carbon dioxide from the patient and replacing it with oxygen. The oxygenated blood is returned to the patient through one of the cannula. When extracorporeal blood flow is to be cut off, typically the machinery is left connected or withdrawn. A convenient way of disconnecting the patient from the ECMO circuit while providing an easy means to reattach to the patient would be desirable but is currently unavailable.

BRIEF SUMMARY OF THE INVENTION

The present invention relates to the discovery of a hemostatic plug apparatus that has a collection chamber of larger diameter than the distal end of the ECMO cannula, a hemostatic membrane and a hemostatic sealing cap overcomes the problems of using cannulas not previously addressed. While it is clear that there is a great advantage of use in an ECMO system, the teaching herein makes it clear that the device may have many other applications other than in an ECMO system.

Accordingly, in one embodiment of the present invention there is a hemostatic plug apparatus for temporarily and hemostatically sealing a catheter or cannula in an extracorporeal membrane oxygenation (ECMO) system comprising:
  a) a collection chamber having a proximal and a distal end, the proximal end adapted to be inserted in the distal end of the ECMO catheter and a distal end adapted to position a hemostatic membrane and receive a hemostatic locking cap;
  b) a hemostatic membrane; and
  c) a hemostatic locking cap adapted to seal the distal end of the collection chamber.

DETAILED DESCRIPTION OF THE INVENTION

Figure 1:
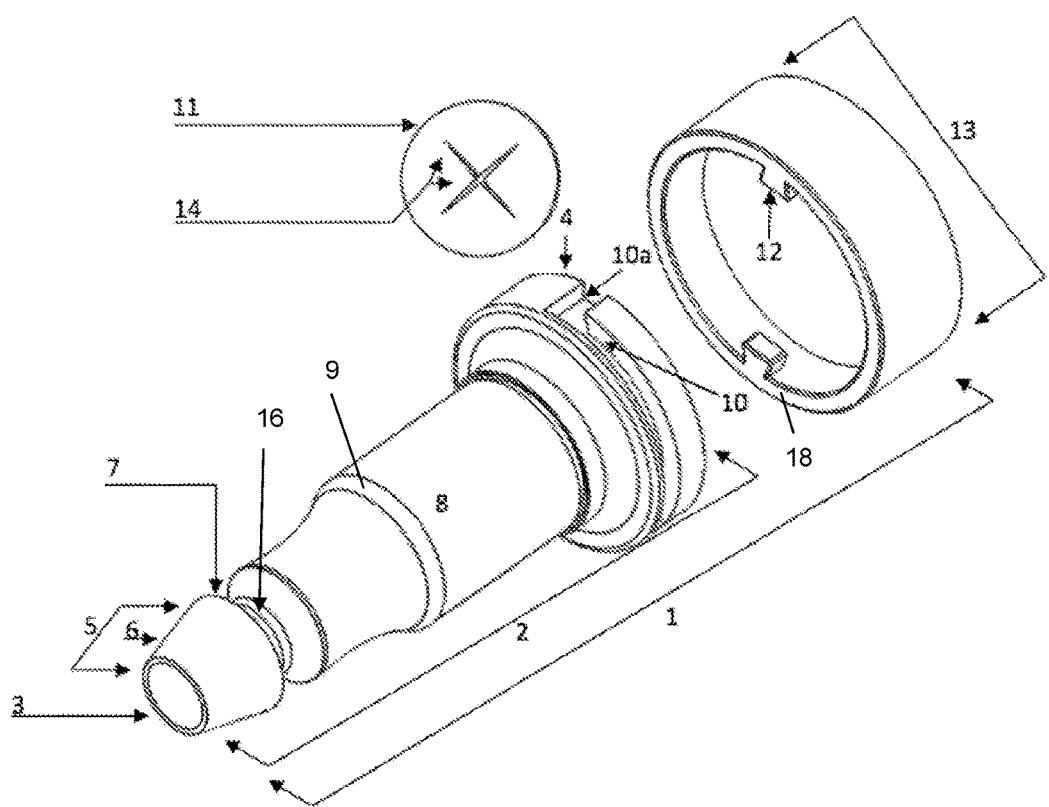
FIG. 1 is an exploded view of the present invention hemostatic plug.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

Definitions

The terms "about" and "essentially" mean ±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto.

Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "hemostatic plug apparatus" refers to a device for sealing a cannula hemostatically and delivering or receiving blood or other liquid from a patient. In one embodiment it is a hemostatic plug designed for use specifically with the cannulas of an ECMO system. The plug apparatus is designed to be temporarily sealed both in a sterile and hemostatic manner. In the case of the present invention it is by use of a locking cap. A hemostatic membrane allows removal of the cap and access to the patient's blood circulation on or off ECMO.

As used herein the term "temporarily" refers to the ability to close off the plug apparatus and use it in the ECMO or other system followed by resealing and being able to repeat the process as necessary. In this invention one embodiment is a locking cap which seals the hemostatic membrane off from the environment in a clean, sterile hemostatic way.

As used herein the term "hemostatically sealing or plug" refers to a seal which prevents the leakage of blood from or to any device or apparatus. The apparatus of the invention is hemostatically sealed in that it performs the function of creating an access port that is sealed in terms of letting blood in or out of an ECMO catheter.

As used herein the term "ECMO catheter or cannula" refers to one of the two catheters or cannulas normally utilized with an ECMO process, one for removing blood one for replacing it. In general this is any of the type of catheter or cannula that handles blood in or out of the body.

As used herein the term "ECMO system" refers to extracorporeal membrane oxygenation equipment including machines, catheters (cannula), pumps, etc associated with ECMO processes.

As used herein the term "collection chamber" refers to a tubular device having a diameter larger than the tubing diameter that it is being utilized with. As shown in the figures by creating a chamber with a volume and greater surface area it allows the distribution of blood pressure in the device over a broader surface, which in turn allows for greater and quicker hemostasis in addition to what the hemostatic membrane provides. The collection chamber has a proximal end (closest to the patient) and a distal end (farthest from the patient). The proximal end is designed to fit into the distal end of one of the cannula or catheters inserted into a patient. The proximal end of the plug apparatus is designed to be a static insertion that is not continually inserted and removed. It can have a tapered configuration in one embodiment, which allows the connection design at the proximal end to be used with various diameter catheters e.g. ⅜ to ½ inch lumen or diameter. The proximal end can be shaped for easy insertion into the lumen of the catheter but can also have a locking shape (as is well known in the art) for keeping the plug apparatus in place once inserted into the tubing. The figures depict one such embodiment of a proximal end. The design is to be hemostatic and sterile during use.

The distal end of the collection chamber is adapted to position a sealed hemostatic membrane. It is also adapted to receive a cap which locks in place and prevents contamination of the exposed hemostatic membrane but is openable during desired use. The collection chamber can be clear, translucent or opaque, though some view of the contents is desirable; therefore any medical grade material that is sufficiently stiff can be utilized. One skilled in the art can select the types of materials to be utilized in view of the disclosure herein that fulfills the requirement of being compatible and safe with exposure to human blood including biocompatible plastics and the like.

As used herein the term "hemostatic membrane" refers to a medical seal for insertion of additional devices such as wires, catheters and the like, which creates a hemostatic seal, both with, and without devices passing though them. In one embodiment, the opening is star shaped, which will adapt to insertion of various diameter medical devices for connection to the hemostatic plug. The hemostatic membrane is of a diameter that fits into the larger diameter of the collection chamber; it can be made of any medical grade material, such as medical grade silicone that will create a seal, it can be used with inserting other devices such as wires or diagnostic catheters, sheaths and the like, remain sterile and create a hemostatic seal in the star or other opening. It can be adapted, e.g. by tapering, to accept a plurality of different size devices such as wires, sheaths, disposable catheters and the like. In one embodiment it can allow devices up to 19 French in size.

As used herein the term "locking cap" refers to a hemostatically and sterile cap for covering the hemostatic membrane at the distal end of the collection chamber. Various types of caps can be utilized such as screw caps and the like. In one embodiment there is a slot on the distal end of the chamber wherein the cap has tabs which fit in the slot and lock with a twisting motion, in addition to a silicone backing on the inside of the cap. A tab and slot type locking cap configuration is shown in the figures and further embodiments will become evident to those skilled in the art in view of the present disclosure. The locking cap can be made of any rigid, materials as is the rest of the hemostatic plug including plastic of a medical grade and the like.

The manufacture of the device can be by any means compatible with the shape and materials utilized. Wherein the device is manufactured of medical grade plastic, manufacture can be by molding, casting or the like by those methods well known in the art for fabrication of plastic medical devices. Likewise, other materials chosen such as metals can be likewise manufactured by means well known in the art in view of the description of the device herein.

DETAILED DESCRIPTION OF THE DRAWINGS

Figure 4:
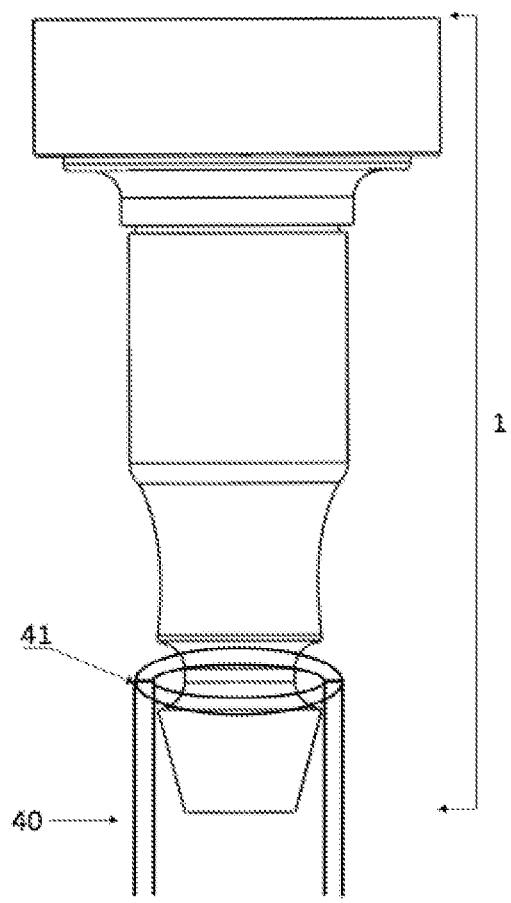
FIG. 4 is a hemostatic plug connected to the distal end of an ECMO cannula.
Figure 5:
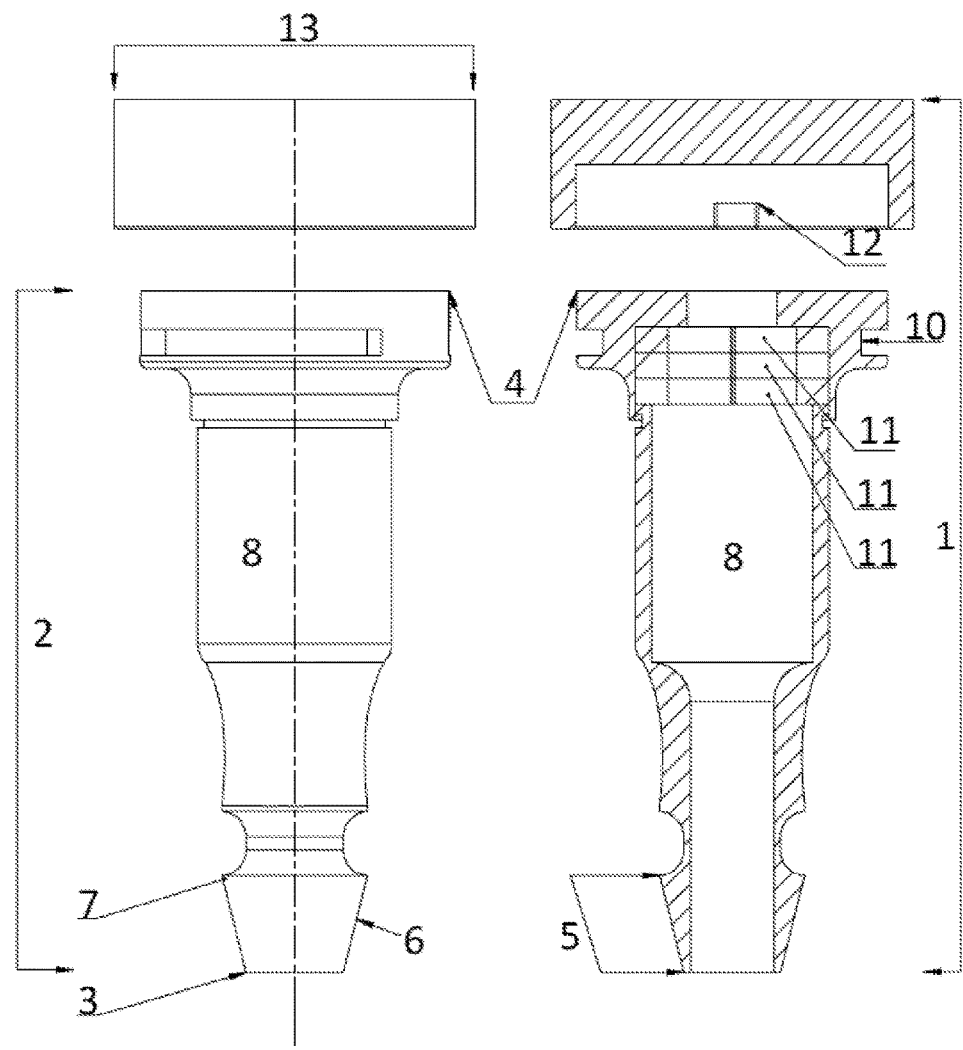
FIG. 5 is a transverse cross-sectional view of the hemostatic plug.

Now referring to the drawings, FIG. 1 is an exploded view of the hemostatic plug apparatus of the present invention. In this view, the hemostatic plug apparatus 1 is broken down in a perspective view into its parts. The collection chamber 2 consists of a proximal end 3 and a distal end 4 with a chamber 8 therebetween. The chamber 8 may include a middle shoulder 9 between ends 3 and 4. As seen in FIGS. 1, 4 and 5, the chamber 8 is a continuous enclosure around a longitudinal axis thereof (i.e. no side inlets therein) such that the fluid flows between the distal end 4 and the proximal end 3. The collection chamber proximal end 3 has a catheter connection 5 which is tapered 6 and has a ridge 7 defined by an outer annular recess 16 (FIG. 1) for holding the catheter on the proximal end 3. The chamber 8 itself is the portion of the plug with a diameter larger than the tubing or cannula it is attached to. The collection chamber distal end 4 is fitted with one or more hemostatic membranes 11 and notched 10 to receive a radially inwardly extending tab 12 of slot locking cap configuration cap 13. Each hemostatic membrane 11 has star slit 14 for inserting a wide range of diameters of catheters, sheaths, wires and the like for diagnostic purposes.

Figure 2:
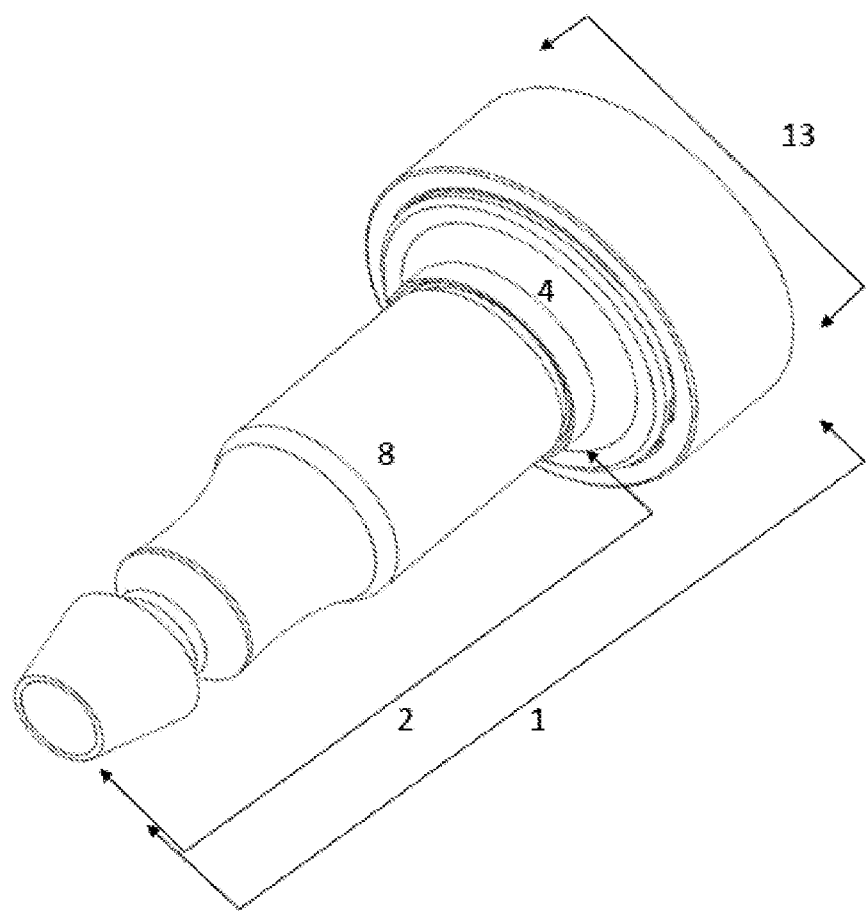
FIG. 2 is an assembled view of the ECMO hemostatic plug.
Figure 3:
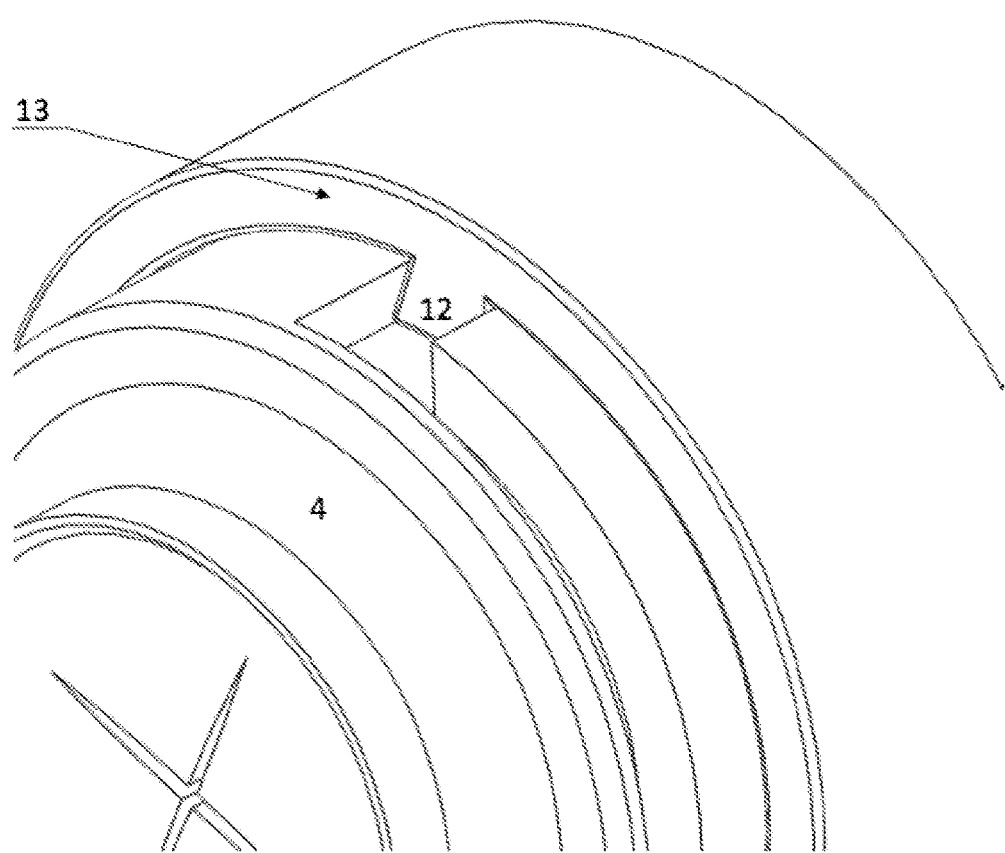
FIG. 3 is a perspective view of a hemostatic plug locking tab and slot locking cap.

FIG. 2 is the assembled hemostatic plug apparatus 1. FIG. 3 shows the embodiment of the tab 12 and slot locking cap configuration cap 13 is fitted with tab 12 which fits into slot 10. The tab 12 is preferably located at or near an annular edge 18 of the cap 13. When tab 12 reaches the bottom of slot 10 the slot locking cap configuration cap 13 can be twisted, rotating tab 12 in a notch portion 10a of the slot 10.

FIG. 4 depicts the hemostatic plug apparatus 1 of the present invention with its collection chamber proximal end 3 being inserted into an ECMO cannula 40 distal end 41; it is shown in the process of the slot locking cap configuration cap 13 being placed on the distal end 41.

FIG. 5 depicts a cross sectional view of the hemostatic plug with the hemostatic membrane 11 housed within the distal end of the collection chamber 4.

Those skilled in the art to which the present invention pertains may make modifications resulting in other embodiments, employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the Applicant.

What is claimed is:

1. A hemostatic plug apparatus for sealing a catheter in an extracorporeal membrane oxygenation (ECMO) system, comprising:
    a collection chamber having a proximal end, a distal end, and a middle shoulder therebetween,
        the proximal end of the collection chamber being a catheter connection adapted to be inserted in the ECMO catheter, the catheter connection being tapered to allow insertion in a range of ECMO cannulas or tubing having distal ends of various diameters, and having a ridge defined by an outer annular recess in the proximal end that is configured to receive a distal end of the ECMO catheter, and
        the distal end of the collection chamber having an annular slot extending at least partially therearound, the annular slot having a notch portion,
        wherein the collection chamber is a continuous enclosure around a longitudinal axis thereof;
    a first hemostatic membrane disposed entirely within the distal end of the collection chamber;
    a second hemostatic member disposed in the distal end of the collection chamber;
    a hemostatic locking cap adapted to seal the distal end of the collection chamber and enclose the first and second hemostatic membranes within the collection chamber, the hemostatic locking cap having a radially inwardly extending tab located at or near an annular edge of the hemostatic locking cap; and
    wherein the annular slot at the distal end of the collection chamber is sized to receive the radially inwardly extending tab of the hemostatic locking cap via the notch portion thereof, thereby allowing the hemostatic locking cap to twist with respect to the collection chamber to seal the hemostatic membrane in the collection chamber.

2. The hemostatic plug apparatus according to claim 1, wherein each of the first and second hemostatic membranes is constructed of medical grade silicone.

3. The hemostatic plug apparatus according to claim 1, wherein the tapered catheter connection is adapted to be inserted in a catheter having a diameter from about $3/8$ inch to about $1/2$ inch at a distal end.

4. The hemostatic apparatus according to claim 1, wherein each of the first and second hemostatic membranes is adapted to accept a plurality of different size devices by having a star pattern opening.

5. The hemostatic plug apparatus according to claim 4, wherein each of the first and second hemostatic membranes is adapted to accept at least one of the group comprising wires, sheaths and diagnostic catheters.

6. The hemostatic plug apparatus according to claim 4, wherein each of the first and second hemostatic membranes is adapted to accept a device up to 19 French.

7. The hemostatic plug apparatus according to claim 4, wherein the collection chamber distal end has an opening exposing the star pattern opening.

* * * * *